(12) United States Patent
Yarema et al.

(10) Patent No.: US 11,015,215 B2
(45) Date of Patent: May 25, 2021

(54) USE OF HIGH FLUX SCFA-DERIVATIZED MONOSACCHARIDES IN RECOMBINANT GLYCOPROTEIN PRODUCTION

(71) Applicant: The Johns Hopkins University, Baltimore, MD (US)

(72) Inventors: Kevin J. Yarema, Woodstock, MD (US); Udayanath Aich, Cambridge, MA (US); Ruben T. Almaraz, Davis, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/593,499

(22) Filed: Jan. 9, 2015

(65) Prior Publication Data

US 2015/0191761 A1    Jul. 9, 2015

Related U.S. Application Data

(60) Provisional application No. 61/925,333, filed on Jan. 9, 2014.

(51) Int. Cl.
| | |
|---|---|
| *C12P 21/00* | (2006.01) |
| *C07K 16/00* | (2006.01) |
| *C07K 14/61* | (2006.01) |
| *C12N 9/18* | (2006.01) |
| *G01N 33/68* | (2006.01) |

(52) U.S. Cl.
CPC ............ *C12P 21/005* (2013.01); *C07K 14/61* (2013.01); *C07K 16/00* (2013.01); *C12N 9/18* (2013.01); *C12Y 301/01008* (2013.01); *G01N 33/68* (2013.01); *C07K 2317/14* (2013.01); *C07K 2317/41* (2013.01)

(58) Field of Classification Search
None
See application file for complete search history.

(56) References Cited

U.S. PATENT DOCUMENTS

2008/0206246 A1* 8/2008 Ravetch ........... A61K 39/39516
424/134.1

OTHER PUBLICATIONS

Almaraz et al. Biotechnology and Bioengineering vol. 109, pp. 992-1006; publication date: Apr. 2012.*
Meanwell. J Med Chem vol. 54, pp. 2529-2591. publication year: 2011.*

* cited by examiner

*Primary Examiner* — Katherine Peebles
(74) *Attorney, Agent, or Firm* — Mintz Levin Cohn Ferris Glovsky and Popeo, P.C.; Peter F. Corless

(57) ABSTRACT

Methods of glycoprotein production employing monosaccharides capable of producing a global increase in flux through the sialic acid pathway are provided.

8 Claims, 5 Drawing Sheets

Ctrl   +PNGase F   +Sialidase

USE OF HIGH FLUX SCFA-DERIVATIZED MONOSACCHARIDES IN RECOMBINANT GLYCOPROTEIN PRODUCTION

RELATED APPLICATION

The present application claims priority to, and the benefit under 35 U.S.C. § 119(e) of U.S. provisional patent application No. 61/925,333, entitled "Use of High Flux SCFA-Derivatized Monosaccharides in Recombinant Glycoprotein Production," filed Jan. 9, 2014. The entire contents of the aforementioned patent application are incorporated herein by this reference.

STATEMENT REGARDING FEDERALLY SPONSORED RESEARCH OR DEVELOPMENT

This invention was made with government support under grant no. CA112314 awarded by the National Institutes of Health. The government has certain rights in the invention.

BACKGROUND OF THE INVENTION

Recombinant glycoproteins currently comprise a global market in the tens of billions of dollars ($109 billion according to recent industry reports, e.g., imarcgroup.com) that has been growing steadily over the past several years with continued prospects for growth. Given such a large market, particularly in therapeutics, it is imperative that glycosylation be understood and properly controlled during the production process.

Monoclonal antibody (mAbs) production (as reviewed in Stadlmann et al. J. Clin. Immunol. 30: 15-19) exemplifies the importance of improved understanding of glycosylation. For mAbs to have optimal activity in ADCC (antibody-dependent cell cytotoxicity) applications (e.g., cancer therapy) they should lack proximal fucose and terminal sialylation (Scallon et al. Mol Immunol. 44: 1524-34; Nimmerjahn et al. Proc Natl Acad Sci USA 104: 8433-7). By contrast, for effective anti-inflammatory activity (e.g., for IVIg (intravenous Ig) therapy), sialic acid is required (Anthony et al. Proc Natl Acad Sci USA 105: 19571-8). Finally, when inappropriate glycan patterns or individual structures appear on mAbs, they can lead to severe immune responses including anaphylactic shock and patient death (Chung et al. N Engl J Med 358: 1109-17). Clearly, it is critical—at a minimum—to avoid harm with respect to the glycosylation of these therapeutics, and beyond that, there are important opportunities to improve product quality and efficacy through optimization of glycosylation.

SUMMARY OF THE INVENTION

The current invention is based, at least in part, upon the discovery that glycoprotein production can be improved through the use of certain short-chain fatty acid (SCFA)-derivatized monosaccharides that are capable of increasing sialic acid pathway flux. Exemplary SCFA-derivatized monosaccharides that increase sialic acid pathway flux include the following:

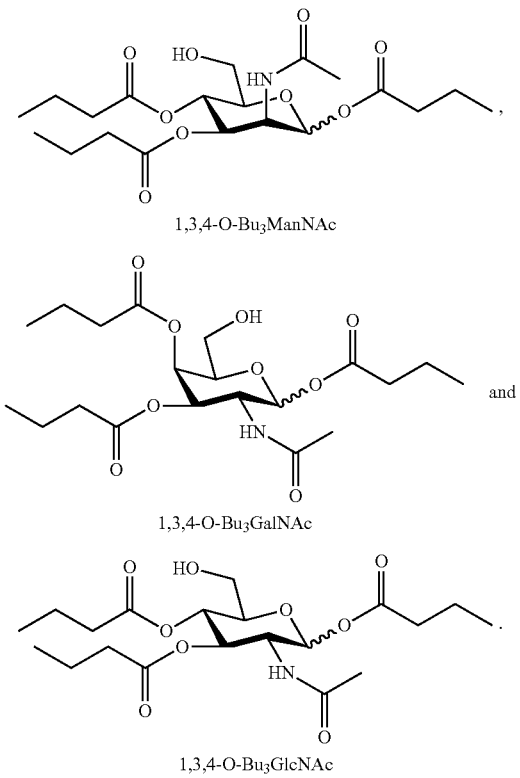

The current invention is based, at least in part, upon the discovery that glycoprotein production can be improved through the use of certain short-chain fatty acid (SCFA)-derivatized monosaccharides, in particular tributanoylated hexosamines with two critical, non-obvious structure-activity relationships (SAR) as illustrated: (i) An unmodified C6-OH group and (ii) ester-linked butyrate groups at the C1, C3, and C4 positions. When the core monosaccharide is a ManNAc moiety, flux through the sialic acid pathway is increased, improving the extent and uniformity of glycoprotein sialylation; the other two cores sugars (GlcNAc and GalNAc) serve as feedstocks for ManNAc inside a cell as well as influence the degree of branching of N-glycans, which can affect the activity of a glycoprotein. More detailed structures of exemplary monosaccharides for use in the methods of the invention are presented below.

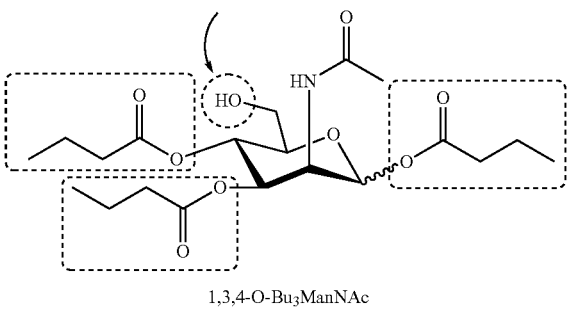

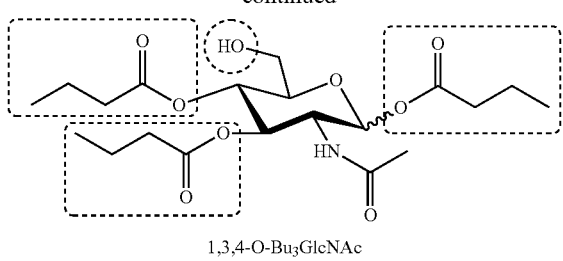

1,3,4-O-Bu₃GlcNAc

Ester-linked, butanoyl-modified C1-, C3-,
and C4-OH positions

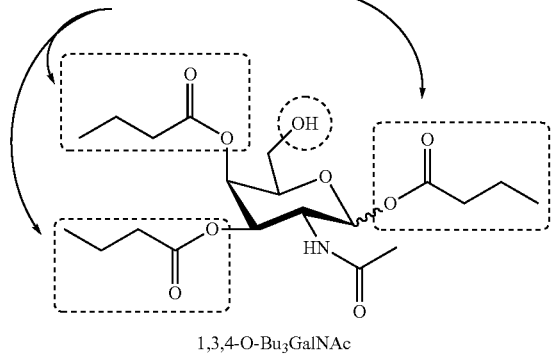

1,3,4-O-Bu₃GalNAc

In one aspect, for example, when a monosaccharide modified with a non-natural N-acyl group (indicated by the "R groups" in the accompanying illustration) that is incorporated into the glycoprotein-displayed glycan, the invention provides a method for producing a glycoprotein that possesses novel biological properties such as improved half-life, reduced toxicity and/or altered immunogenicity, the method involving contacting a protein, under conditions that allow glycoprotein formation to occur, with one or more of the following compounds that are capable of modifying flux through glycosylation pathways efficiently and without deleterious cytoxicity associated with peracylated monosaccharide analogs:

Non-natural N-acyl moiety

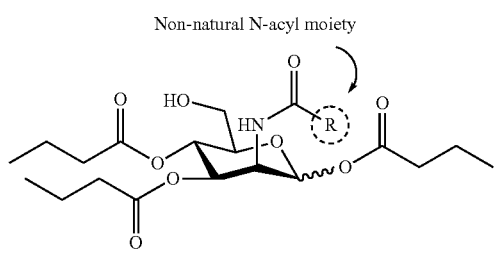

"R"-modified
1,3,4-O-Bu₃ManNAc

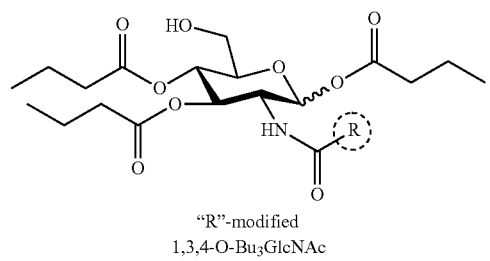

"R"-modified
1,3,4-O-Bu₃GlcNAc

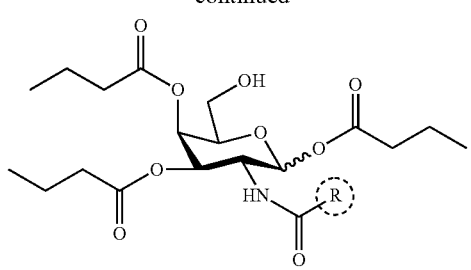

"R"-modified
1,3,4-O-Bu₃GalNAc where R includes one of the following moieties reported to be using in metabolic glycoengineering (—CH₃ constitutes the natural core sugar):

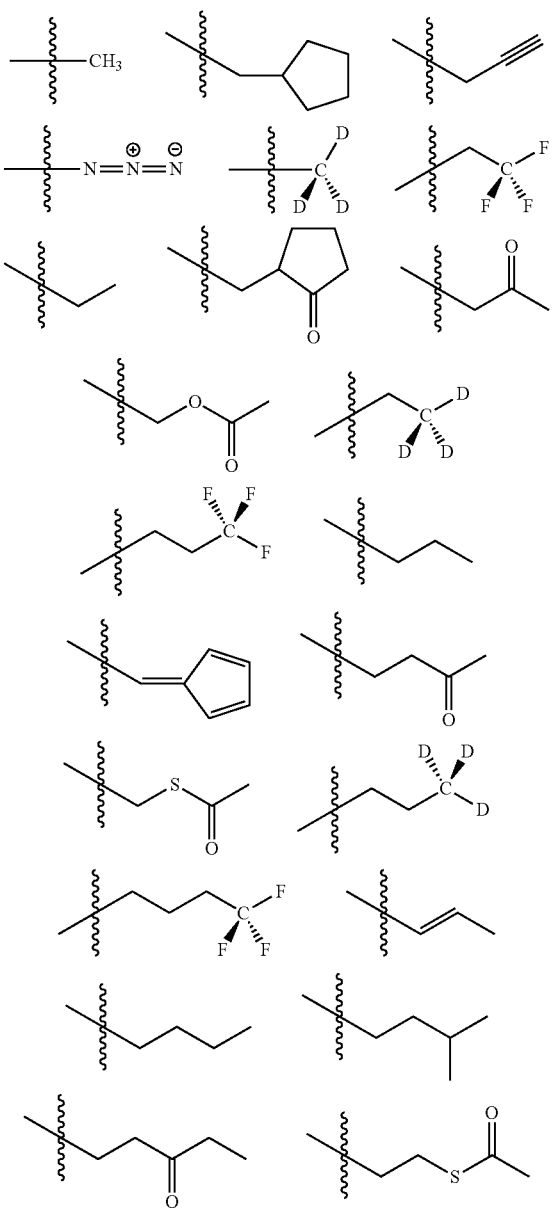

-continued

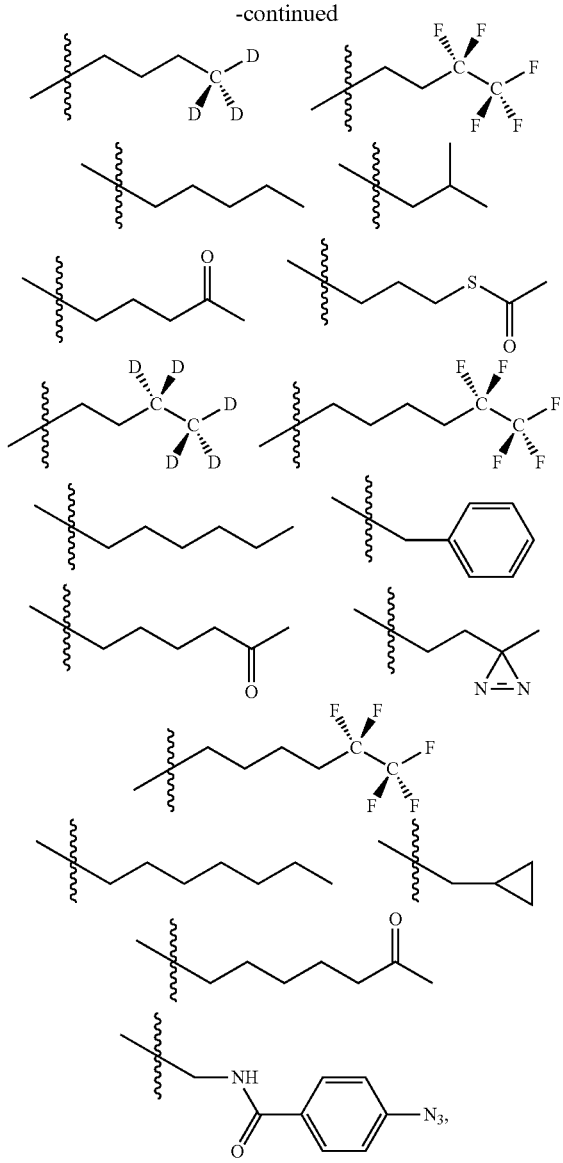

F = $^{18}$F or $^{19}$F such that the resulting glycoprotein possesses improved half-life, reduced toxicity and/or altered (optionally, reduced) immunogenicity as compared to an appropriate control glycoprotein that has not been contacted with the compound.

In certain embodiments, the glycoprotein is an antibody, an enzyme or a hormone. In one embodiment, the glycoprotein is an antibody component of intravenous immunoglobulin (IVIG) therapy. Optionally, the glycoprotein is butyl-cholinesterase enzyme. In one embodiment, the glycoprotein is human growth hormone (HGH).

In another embodiment, the glycoprotein is produced in a mammalian cell. Optionally, the mammalian cell is a Chinese hamster ovary (CHO) cell.

In a related embodiment, the glycoprotein possesses increased sialylation as compared to the control glycoprotein.

Another aspect of the invention provides a method for increasing the half-life, reducing the toxicity and/or reducing the immunogenicity of a glycoprotein produced in a mammalian cell, the method involving contacting a mammalian cell with one or more of the following compounds which are capable of globally increasing flux through the sialic acid pathway:

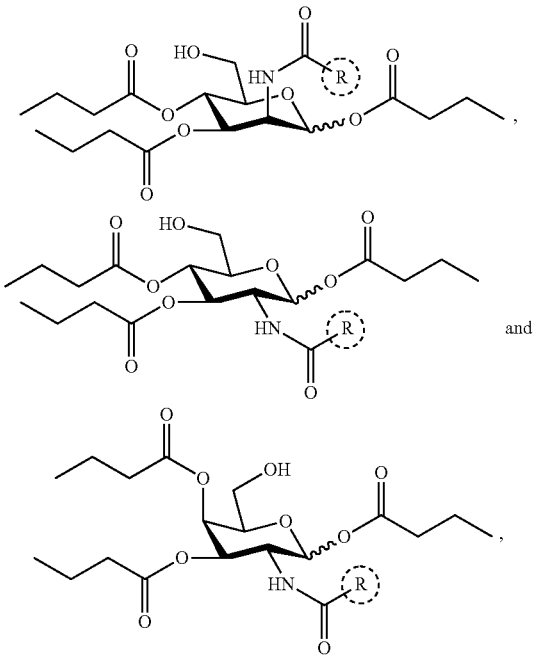

where R is selected from the following:

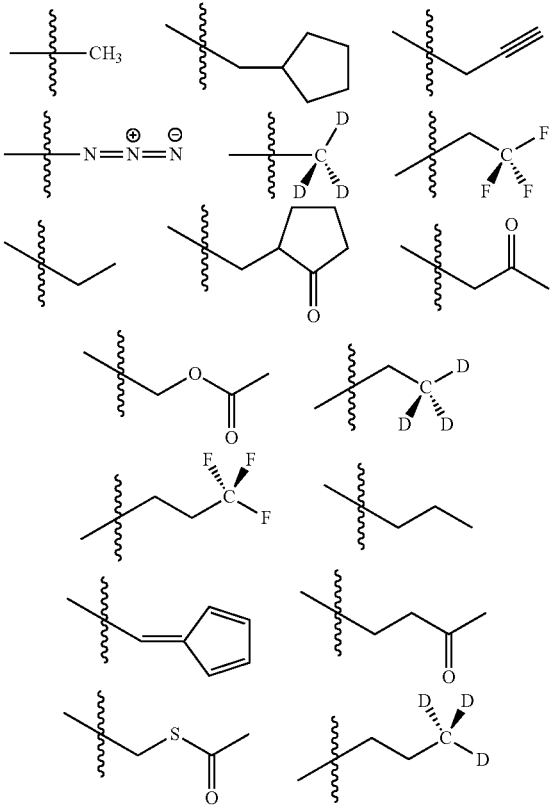

-continued

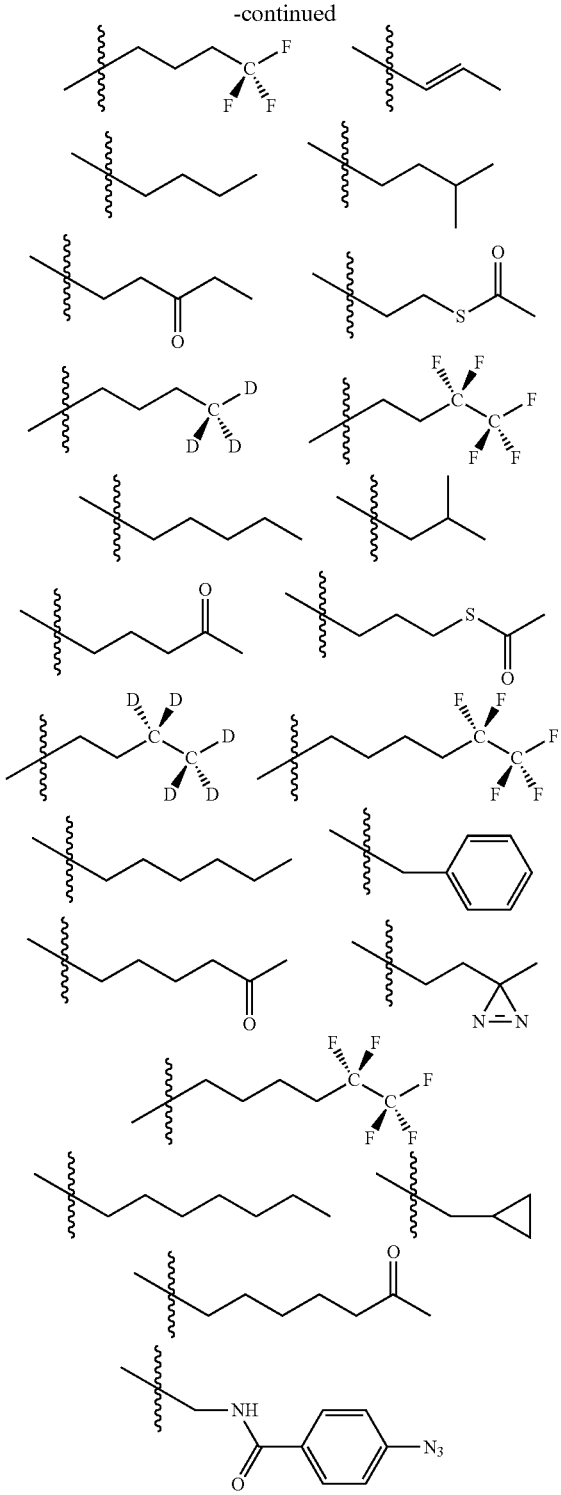

F = $^{18}$F or $^{19}$F under conditions that allow glycoprotein production to occur in the mammalian cell, thereby increasing the half-life, reducing the toxicity and/or reducing the immunogenicity of the glycoprotein produced in the mammalian cell, as compared to an appropriate control glycoprotein produced in a mammalian cell not contacted with the compound.

A further aspect of the invention provides a method for identifying a glycoprotein possessing increased half-life, reduced toxicity and/or reduced immunogenicity, the method involving expressing a glycoprotein in a mammalian cell contacted with one or more of the following compounds:

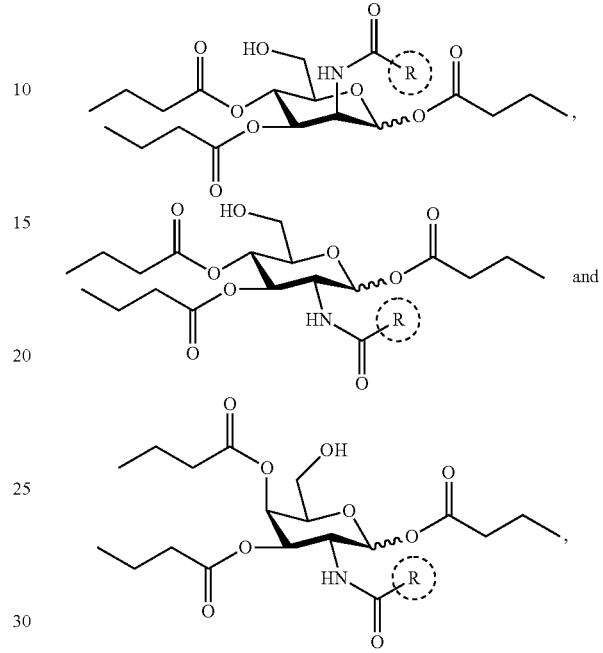

where R is selected from the following:

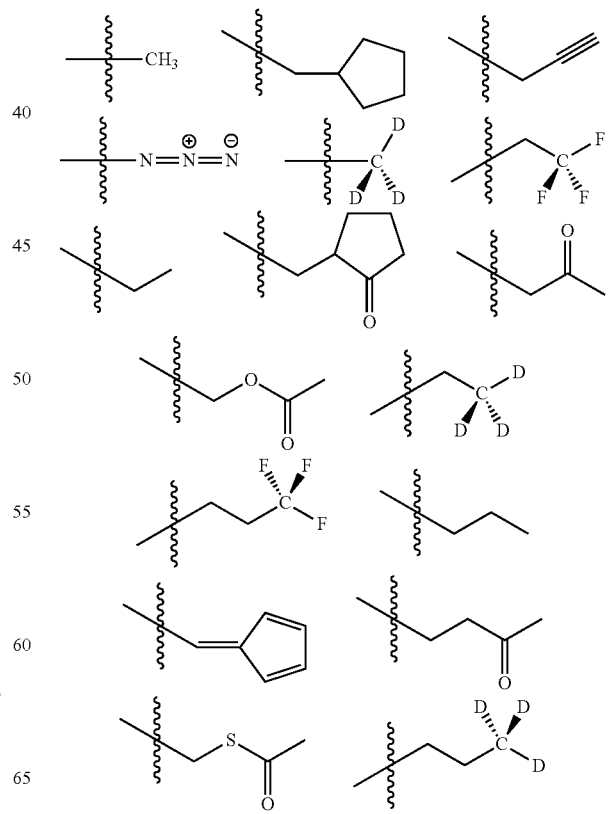

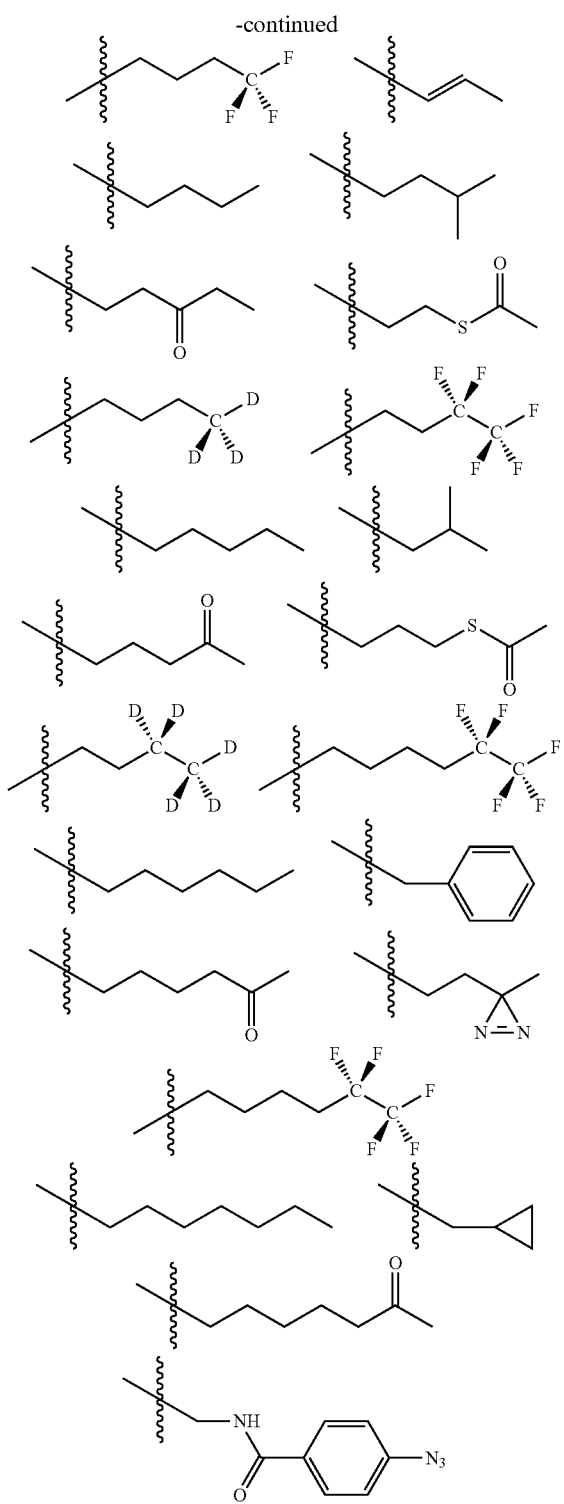

F = $^{18}$F or $^{19}$F under conditions that allow glycoprotein production to occur in the mammalian cell; isolating the expressed glycoprotein produced by the mammalian cell; and characterizing the half-life, toxicity and/or immunogenicity of the isolated expressed glycoprotein, where the isolated expressed glycoprotein is identified to possess increased half-life, reduced toxicity and/or reduced immunogenicity as compared to an appropriate control glycoprotein expressed in a mammalian cell not contacted with the compound, thereby identifying a glycoprotein that possesses increased half-life, reduced toxicity and/or reduced immunogenicity as compared to a glycoprotein expressed in a mammalian cell not contacted with the compound.

In addition, deuterated compounds of the methods of the present invention can be used to quantitatively monitor biosynthetic incorporation of the compound into the glycans of a glycoprotein (e.g., by mass spectrometry) and the fluorinated analogs allow imaging of the glycoproteins (e.g., by NMR for the dominant $^{19}$F isotope or by PET for $^{18}$F. Such applications can allow the pharmacokinetics of a therapeutic glycoprotein to be monitored in vivo.

In one such aspect, the invention provides a method for monitoring the incorporation of a compound into a glycoprotein that involves contacting a protein with a compound that is

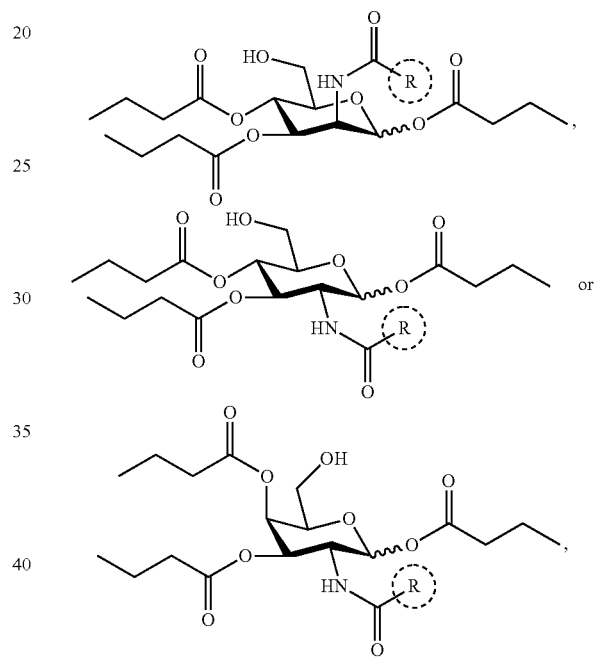

where R is

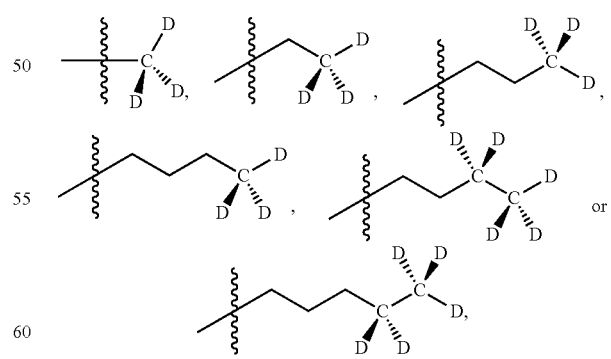

under conditions that allow for glycoprotein formation to occur between the protein and the compound; and measuring the amount of the compound in the glycoprotein as a means of monitoring the incorporation of the compound into the glycoprotein.

In one embodiment, such measuring is quantitative and optionally involves mass spectrometry.

In another aspect, the invention provides a method for imaging a glycoprotein that involves contacting a protein with a compound that is

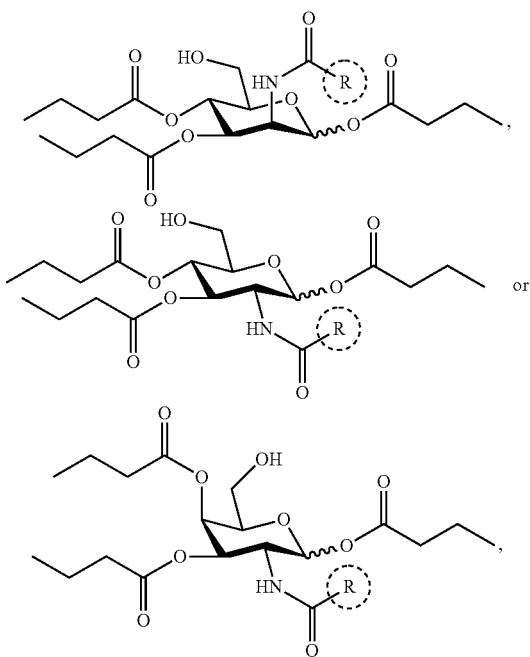

where R is

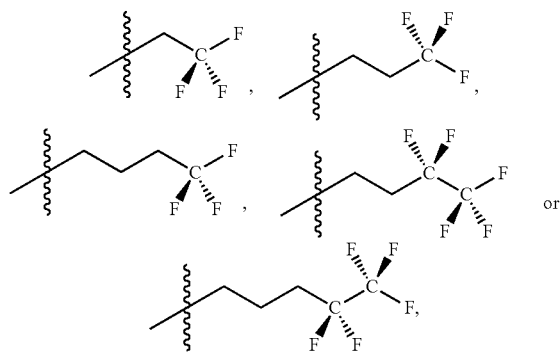

where F is $^{18}$F or $^{19}$F, under conditions that allow for glycoprotein formation to occur between the protein and the compound; and detecting the F groups of the glycoprotein as a means of imaging the glycoprotein.

In one embodiment, F is $^{19}$F. In a related embodiment, detecting involves measurement of nuclear magnetic resonance (NMR).

In another embodiment, F is $^{18}$F. In a related embodiment, detecting involves measurement of positron emission tomography (PET).

In one embodiment, the imaging is performed in vivo.

In another embodiment, the glycoprotein is a therapeutic glycoprotein administered to a subject. Optionally, the pharmacokinetics of the therapeutic glycoprotein are measured in the subject.

DETAILED DESCRIPTION OF THE INVENTION

Figure 1:
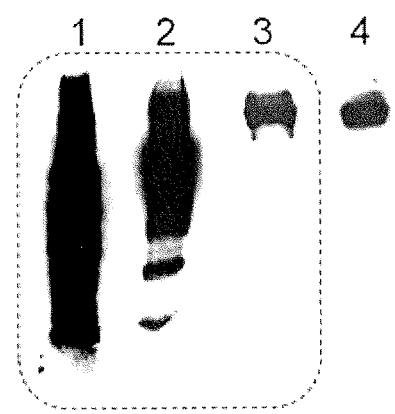
FIG. 1 shows immunopurified treated integrin α4β1. Whole cell lysate from cells treated with 100 μM 1,3,4-O-Bu$_3$ManNAz for 24 hours and "click" chemistry biotinylated were probed with streptavidin (lane 1), and from the same whole cell lysate, integrin α4β1 was immunopurified using human anti-MUC1 antibody and probed with streptavidin (lane 2). Immunopurified integrin α4β1 was again incubated with the human anti-MUC1 antibody and re-purified (lane 3). The band in lane 4 was the same sample as lane 3 but probed with anti-human integrin α4.

The present invention relates, at least in part, to the discovery that globally effecting increased flux through the sialic acid pathway, via use of certain compounds described herein, can be used to improve glycoprotein production (especially large-scale glycoprotein production, e.g., for therapeutic monoclonal antibodies, enzymes, etc.), by providing glycoproteins with improved half-life, reduced toxicity (to a cell and/or organism/subject) and/or reduced immunogenicity.

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

As used herein, the term "recombinant polynucleotide", which is used interchangeably with "isolated polynucleotide", means a nucleic acid polymer such as a ribonucleic acid or a deoxyribonucleic acid, either single stranded or double stranded, originating by genetic engineering manipulations. A recombinant polynucleotide may be a circular plasmid or a linear construct existing in vitro or within a cell as an episome. A recombinant polynucleotide may be a construct that is integrated within a larger polynucleotide molecule or supermolecular structure, such as a linear or circular chromosome. The larger polynucleotide molecule or supermolecular structure may be within a cell or within the nucleus of a cell. Thus, a recombinant polynucleotide may be integrated within a chromosome of a cell.

The term "half-life," "serum half-life" or "plasma half-life" as used herein is intended to indicate the amount of time that is required for the concentration or amount of glycoprotein when in the body to be reduced to exactly one-half of a given concentration or amount. In certain embodiments, the glycoproteins of the methods of the invention display significantly longer half lives than appropriate control glycoproteins. For example, the serum half-life of the disclosed molecules can increase by 20%, 30%, 40%, 50%, 60%, 70%, 80%, 90%, 100%, 200%, 300%, 400%, 500%, 750%, 1000%, 1250%, 1500%, 1750%, 2000% or more over the serum half-life of appropriate control proteins/glycoproteins not exposed to the compounds of the methods of the invention.

Reference herein to "toxicity" should be understood as reference to a toxic effect in a cell and/or subject caused by contact with and/or administration of a protein or glycoprotein to the cell and/or subject.

The term "immunogenicity" as used herein refers to a measure of the ability of a protein or glycoprotein of the invention to elicit an immune response (humoral or cellular) when administered to a recipient (e.g., mammalian subject, e.g., a human subject). In certain embodiments, the present invention is concerned with the immunogenicity of recombinant glycoproteins.

A "polypeptide" refers to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present invention in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis (SDS-PAGE).

Glycosylation has a major impact on recombinant glycoproteins with important implications for the increasing therapeutic use of these compounds. Monoclonal antibodies exemplify this concept wherein certain applications (cancer treatment) require minimal sialic acid and fucose while other applications (IVIg) benefit from high levels of sialylation. In addition to building in these desirable properties, care must be taken to avoid glycoforms that lead to severe immune reaction and even patient death. Therefore the quality (defined broadly as the type, extent, and homogeneity) of the glycan moieties of these biologics is of paramount importance. Disclosed herein are the design and implementation of sugar-based agents that improve the quality of these products in an efficient manner.

Hexosamine Supplementation To Improve Product Quality of Recombinant Glycoproteins Used Therapeutically Glycosylation can tune the activity of recombinant glycoproteins. However, product quality issues of glycoproteins also include their pharmacological properties; in general, the higher the degree and uniformity of sialylation, the longer the serum half life becomes. Also, with the notable exception of ADCC, a high level of sialylation does not impede the activity of recombinant glycoproteins. For purpose of the methods of the instant invention, while they may not provide a universal strategy, in most cases the described methods to increase sialic acid production during recombinant glycoprotein production—including antibodies—are beneficial (Raymond et al. 2012).

One strategy to increase sialic acid production was supplementation of the culture system with exogenous ManNAc, the committed intracellular metabolite for supplying the sialic acid biosynthetic pathway with metabolic flux. The benefits of using ManNAc for improving the sialylation of recombinant glycoproteins has been previously described (Yorke et al. 2013), but for the following structures of ManNAc and other analogs, which also possess elevated toxicity.

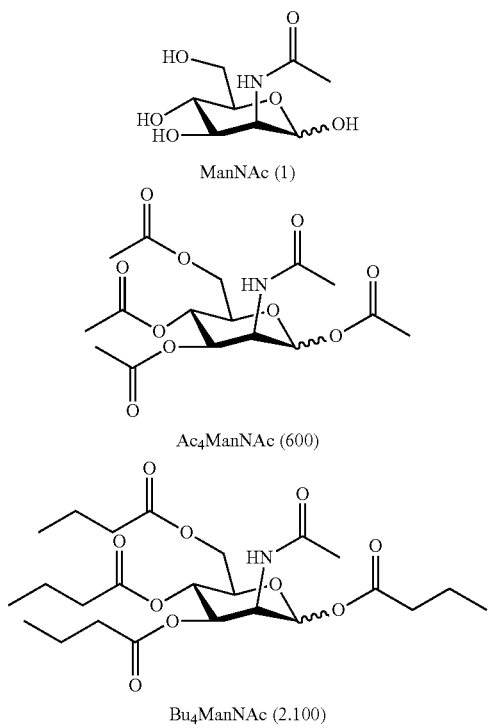

n-Butyrate Supplementation Can Also Improve Recombinant Protein Production

Recombinant protein production can also be improved (for now, unrelated to glycosylation as discussed above) through addition of n-butyrate to a culture system. This SCFA functions as a HDACi, resulting in blocked (or slowed) cell cycle progress, thus allowing the host cells to devote more of their metabolic capacity to production of the recombinant protein rather than to reproducing cellular components during cell replication. For purpose of the improved methods of glycosylation set forth herein, the use of butyrate is compatible with this endpoint (Lamotte et al. 1999). Indeed, the general use of n-butyrate for recombinant protein production has been previously described (Arden et al. 2004; Sung et al. 2004; Lee et al. 2012; and Chang et al. 2002).

Difficulties of Use of Perbutanoylated ManNAc Compounds in Recombinant Glycoprotein Production Despite the benefits of ManNAc (the exemplary hexosamine discussed immediately above) and n-butyrate for recombinant protein production, they are not widely used. This is at least in part due to the following shared problem: low efficiency of use. ManNAc, for example, is usually present at low micromolar concentrations inside a cell, but has to be supplemented at up to 50 mM to the cell culture media for a robust increase in sialic acid production to take place within a cell. Similarly, high concentrations (~10 mM or higher) of n-butyrate are required to elicit desired cell responses.

One solution tried in an attempt to address both problems was to ester-link four n-butyrate groups to the ManNAc (to form perbutanoylated ManNAc, Bu$_4$ManNAc; this strategy was based on an earlier demonstration that Ac$_4$ManNAc was several hundred fold more efficient than the unmodified sugar (Jones et al. 2004)—longer SCFA rendered the sugar even more lipophilic and increased efficiency further. In this way, both the sugar and SCFA had their hydrophilic membrane-impermeable groups masked and the much more lipophilic hybrid molecule could enter into cells more efficiently. Upon testing this compound, it was indeed much more efficient (~2,100-fold when sialic acid production was the endpoint being measured (Kim et al. 2004)) and it slowed cell growth within 2 or 3 days of treatment (Sampathkumar et al. 2006). Basically, both the core sugar and n-butyrate (which tend to be generated rapidly within a cell by esterase processing (Mathew et al. 2012)) exhibited activities predicted to be beneficial for recombinant glycoprotein treatment. However, beyond short time periods of 2 to 3 days—e.g., up to and within two weeks, the host cells died from Bu$_4$ManNAc treatment (Sampathkumar et al. 2006), rendering this approach unsuited for recombinant glycoprotein production.

Butanoylated ManNAc Analogs Possessing Reduced Cytotoxicity

Overturning 30 years of widespread belief that the biological effects of SCFA-monosaccharide hybrid molecules such as Bu$_4$ManNAc were solely due to the hydrolysis products (e.g., n-butyrate and ManNAc) of such compounds, the Yarema group demonstrated that the cytotoxicity of Bu$_4$ManNAc was attributed to unanticipated "whole molecule" effects (Campbell et al. 2008; Aich et al. 2008; Elmouelhi et al. 2009; Wang et al. 2009). These effects were enhanced by removal of the ester-linked acyl group from the C1 position of the sugar ring, creating "3,4,6"-modified compounds that are potentially useful for the treatment of several diseases (e.g., cancer (Campbell et al. 2008) and osteoarthritis (Coburn et al. 2013; Coburn et al. 2013)).

In another unexpected result, tri-acylated hexosamine analogs (e.g., tri-butanoylated ManNAc, 1,3,4-O-Bu$_3$ManNAc) lacking a SCFA moiety at the C6 hydroxyl position were discovered to lack "whole molecule" toxicity and other effects that could not be attributed to the core sugar or hydrolyzed n-butyrate (Aich et al. 2008). Rather, 1,3,4-O-Bu$_3$ManNAc provided high levels of flux into the sialic acid pathway (consistent with ManNAc) and in most cell lines exhibited mild growth inhibition (consistent with the HDACi activity of hydrolyzed n-butyrate). There was no literature or scientific precedent at the time for the unexpected finding that removal of one of the n-butyrate groups, and especially the one at the C6 (as compared to other positions, e.g., at C1—where removal exacerbated whole molecule effects instead of dampening them) would provide the high-flux, mild growth inhibition phenotype exhibited by 1,3,4-O-Bu$_3$ManNAc.

1,3,4-O-Bu$_3$ManNAc Has Protein- and Glycosylation-Specific Flux-Driven Activity One problem with the natural sugar ManNAc is that it only increases overall cell surface sialylation by approximately 5 to 10% (secreted glycoproteins likely experience an improvement of similar magnitude); this rather unimpressive level was found to be increased by peracetylated ManNAc (Ac$_4$ManNAc) to approximately 10 to 25% (note the Ac$_4$ManNAc also suffers from drawbacks of Bu$_4$ManNAc, i.e., cytotoxicity over prolonged exposure to cells). By comparison, 1,3,4-O-Bu$_3$ManNAc increased overall sialylation of glycoconjugates by 50 to 75%. So, in this respect it was clearly superior to its peracylated counterparts.

Another way the efficacy of 1,3,4-O-Bu$_3$ManNAc was demonstrated was to probe the individual sites of N-glycosylation using mass spec and glycoproteomics methods (Almaraz et al. 2012). In such studies, the collective measurements described in the above paragraph were not adequate to predict the impact on any particular protein (e.g., the recombinant glycoprotein of interest). This was because these results showed that about ⅓ of glycosylation sites did not respond to analog-driven increases in flux (i.e., the level of sialylation remained unchanged despite increase sialic acid production in the cell), about ⅓ experienced a modest increase (e.g., ≤2-fold), while about ⅓ experience dramatic increases (e.g., of 8-fold or more). Similarly, analysis of the glycans themselves revealed a subset that experienced increased sialylation while other oligosaccharide structures did not (Shah et al. 2013). Such studies revealed that dramatic product quality improvements could be obtained for some, but not all, glycoproteins.

"High Flux" SARs Apply to Additional Hexosamines

The structure activity relationships (SAR) described above for 1,3,4-O-Bu$_3$ManNAc apply for the two other common mammalian hexosamines, GalNAc and GlcNAc (Elmouelhi et al. 2009). More specifically, 1,3,4-O-Bu$_3$GalNAc and 1,3,4-O-Bu$_3$GlcNAc introduce high levels of flux into the GalNAc salvage and hexosamine biosynthetic pathways, respectively, with minimal side effects (e.g., cytotoxicity) compared to their perbutanoylated counterparts Bu$_4$GalNAc and Bu$_4$GlcNAc, their 3,4,6-O-Bu$_3$GalNAc and 3,4,6-O-Bu$_3$GlcNAc tributanoylated counterparts, or peracetylated Ac$_4$GalNAc and Ac$_4$GlcNAc counterparts. These compounds have the ability to alter the N-glycosylation of recombinant glycoproteins as well as intracellular O-GlcNAcylation.

"High Flux" SARs Apply to Non-Natural Core Sugars

The structure activity relationships (SAR) described above for 1,3,4-O-Bu$_3$ManNAc, 1,3,4-O-Bu$_3$GalNAc, and 1,3,4-O-Bu$_3$GlcNAc also apply for N-acyl modified analogs (e.g., azido-analogs 1,3,4-O-Bu$_3$ManNAz, 1,3,4-O-Bu$_3$GalNAz, and 1,3,4-O-Bu$_3$GlcNAz; Almaraz et al 2012), and more generally to any N-acyl modified version of these hexosamines, e.g.,

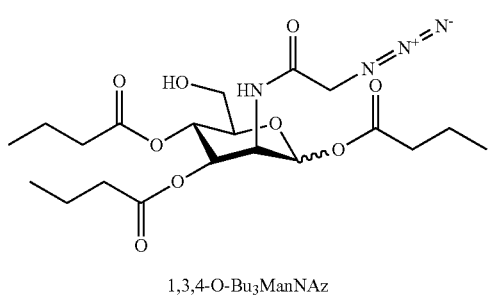

1,3,4-O-Bu$_3$ManNAz

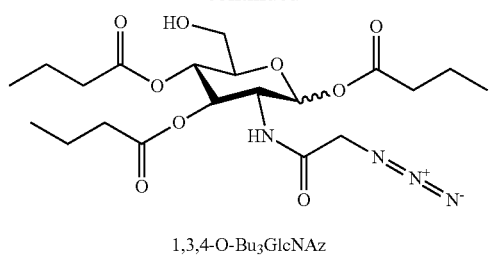
1,3,4-O-Bu₃GlcNAz
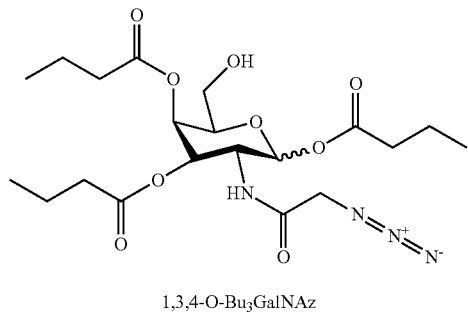
1,3,4-O-Bu₃GalNAz
and more generally to any N-acyl modified version of these hexosamines, e.g.,
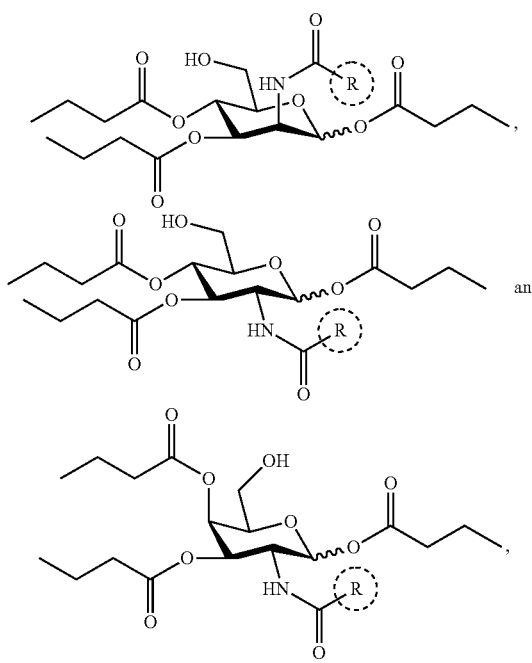
where R is selected from the following:
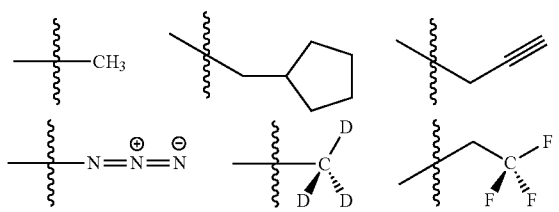
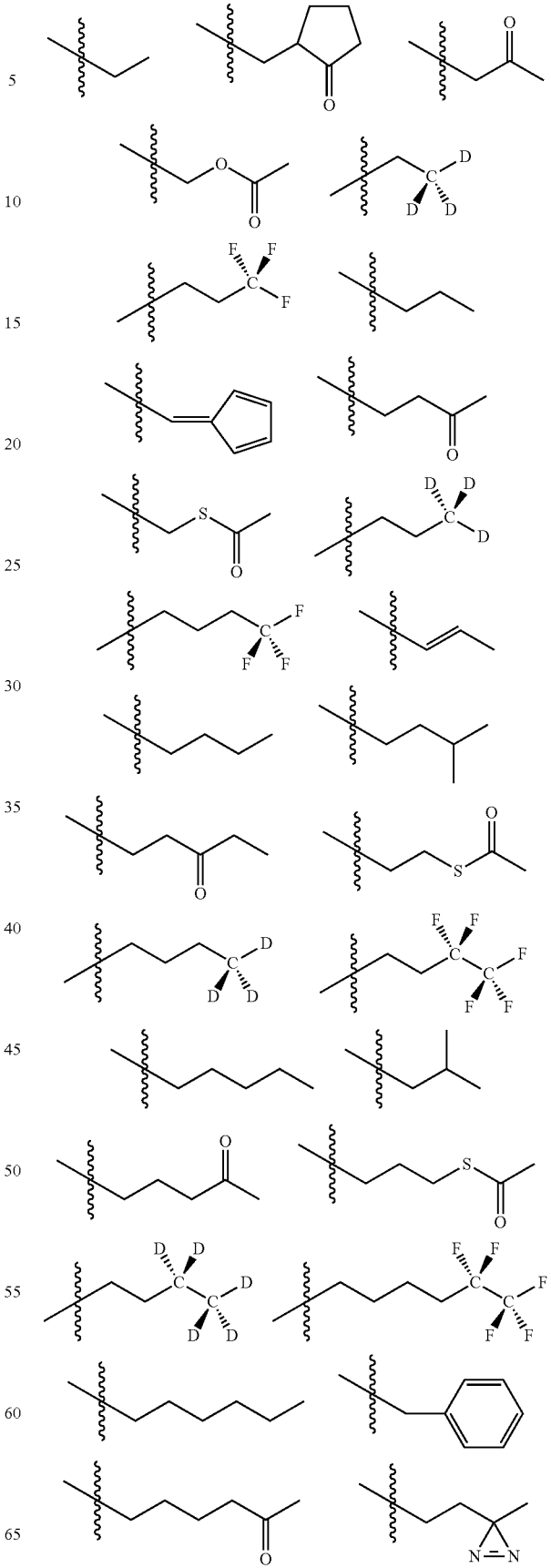

-continued

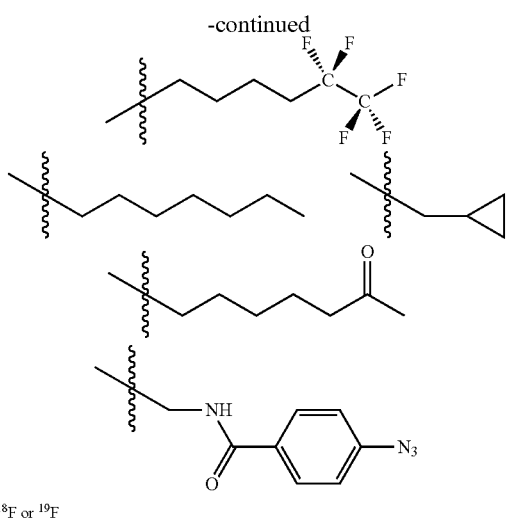

F = $^{18}$F or $^{19}$F

As described herein, this class of compounds can be used to install non-natural chemical properties into recombinant proteins, and as is first described herein with respect to industrial production and/or screening of glycoproteins, to do so efficiently. Further, this technology applies CHO cells, the "workhorse" cell line for recombinant glycoprotein production. Efficient uptake into the collective repertoire of proteins produced by CHO cells was previously established (Almaraz et al. 2012).

Certain SAR of note for the methods of the instant invention were previously described in Aich et al (2008) and Elmouelhi et al (2009).

Glycoprotein Production in Cell Culture

Illustrative of cell cultures useful for the production of proteins are cells of insect or mammalian origin. Mammalian cell systems often will be in the form of monolayers of cells although mammalian cell suspensions may also be used. Mammalian cell systems are often used for glycoprotein production. Illustrative examples of mammalian cell lines include VERO and HeLa cells, Chinese hamster ovary (CHO) cell lines, W138, BHK, COS-7 or MDCK cell lines.

In certain aspects, the methods of the invention involve contacting a protein and/or a mammalian cell with a compound as described herein. In certain embodiments, the compounds of the invention are used at sub-millimolar concentrations in the environment of a cell and/or protein. Exemplary sub-millimolar concentrations for use of the compounds of the invention include 100 μM or less, 50 μM or less, 10 μM or less, 5 μM or less, 4 μM or less, 3 μM or less, 2 μM or less, 1 μM or less, 500 nM or less, 250 nM or less, 100 nM or less, 50 nM or less, 25 nM or less, 20 nM or less, 10 nM or less, 5 nM or less, 4 nM or less, 3 nM or less, 2 nM or less, 1 nM or less, 500 pM or less, 250 pM or less, 100 pM or less, 50 pM or less, 25 pM or less, 20 pM or less, 10 pM or less, 5 pM or less, 4 pM or less, 3 pM or less, 2 pM or less, 1 pM or less, 0.5 pM or less, 0.2 pM or less, 0.1 pM or less, 0.05 pM or less, 0.02 pM or less, 0.01 pM or less, 0.005 pM or less, 0.002 pM or less or 0.001 pM or less, in the environment of the cell and/or protein.

Assay for Total Sialic Acid Production

Jurkat cells (5.0×10$^6$ cells in 10 mL medium) are incubated with a compound of the invention at various concentrations. After three days, the cells (1.0×10$^6$ cells per sample) are lysed by freeze-thaw cycles (three times). The cell lysates are analyzed by using an adapted version of the periodate-resorcinol assay with the periodic acid oxidation step performed on ice to allow quantification of total (i.e., free monosaccharide plus glycoconjugate-bound) sialic acid. For each assay, a standard curve is obtained using N-acetylneuraminic acid (Pfanstiehl, Waukegan, Ill.) for calibration.

Compounds

The compounds of the invention provide high sialic acid flux in mammalian cell glycoprotein expression systems.

The compounds of the invention may have a divergent impact on transcription, and are linked to the interplay between the HDACi and NF-κB activity, which was previously identified as selectively down regulated by these compounds.

As used herein, the term "alkyl" refers to a straight-chained or branched hydrocarbon group containing 1 to 18 (e.g., C1-C-18, inclusive; and any sub-range thereof) carbon atoms. The term "lower alkyl" refers to a C1-C6 alkyl chain. Examples of alkyl groups include methyl, ethyl, n-propyl, isopropyl, n-butyl, sec-butyl, tort-butyl, pentyl (n-, sec-, ten-), and pivaloyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp$^2$ or sp carbons of an alkenyl group and an alkynyl group, respectively, may optionally be the point of attachment of the alkenyl or alkynyl groups.

The term "alkoxy" refers to an —O-alkyl substituent group. The term "ester" refers to a —C(O)O—R, wherein R is as defined herein. An "amido" is an —C(O)NH$_2$, and an "N-alkyl-substituted amido" is of the formula C(O)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cycloalkenyl" refers to a hydrocarbon 3-8 membered monocyclic or 7-14 membered bicyclic ring system having at least one non-aromatic ring, wherein the non-aromatic ring has some degree of unsaturation. Cycloalkenyl groups may be optionally substituted with one or more substituents. In one embodiment, 0, 1, 2, 3, or 4 atoms of each ring of a cycloalkenyl group may be substituted by a substituent. Examples of cycloalkenyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "arylalkyl" means an aryl group that is attached to another group by a $(C_1-C_6)$alkylene group. Arylalkyl groups may be optionally substituted, either on the aryl portion of the arylalkyl group or on the alkylene portion of the arylalkyl group, with one or more substituent. Representative arylalkyl groups include benzyl, 2-phenyl-ethyl, naphth-3-yl-methyl and the like.

As used herein, the term "alkylene" refers to an alkyl group that has two points of attachment. The term "$(C_1-C_6)$ alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH$ ($CH_3$)—), and the like.

The term "arylalkoxy" refers to an alkoxy substituted with aryl.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkane or alkene. Heteroarylalkyl groups may be optionally substituted, either on the heteroaryl portion of the heteroalkyl group or on the alkyl portion of the heteroarylalkyl group, with one or more substituents. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocycloalkenyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include 2-pyrrolinyl, 3-pyrrolinyl, 4H-pyranyl, 2-pyrazolinyl, dihydrofuranyl, dihydrothiophenyl, 2-imidazolinyl, indolinyl and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR), wherein R is as defined herein.

In other embodiments, substituents on any group (such as, for example, alkyl, alkenyl, alkynyl, aryl, arylalkyl, heteroaryl, heteroaralkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucuronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, oxalic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

Features of the Compounds of the Invention

Featured qualities of the compounds used in the methods of the invention include:
(1) The compounds possess bifunctional, dual activity from the sugar (see 2, below) and SCFA (see 3, below) moieties;
(2) One mode of activity derives from the core sugar, which can be natural or non-natural, and custom-designed targeted to various glycosylation pathways;
(3) The other mode of activity derives from ester-linked short chain fatty acids (SCFAs), which are attached to the core sugar to improve cell uptake and then function as HDACi (histone deacetylase inhibitors) to increase recombinant protein yield upon intracellular hydrolysis of the SCFA (in certain embodiments, n-butyrate).
(4) Regioisomeric positioning of the SCFA groups on the sugar "scaffold" is an important design parameter to ensure high flux of the analog into the targeted glycosylation pathway without eliciting deleterious side effects (e.g., apoptosis and cell death) often associated with SCFA-modified hexosamines;
(5) The structure/activity relationships that allow the current compounds to provide non-toxic, high flux properties extend to non-natural hexosamines used in metabolic glycoengineering;
(6) Point (5) above can be exploited to provide the recombinant protein with new properties (e.g., increased half-life, reduced toxicity and/or reduced immunogenicity);
(7) Point (5) can be exploited for site-specific conjugation of second agents to a recombinant protein;
(8) Compared to, e.g., peracetylated hexosamines, the compounds of the methods set forth herein (in addition to having superior biological activity) provide a 3 to 10 fold or higher increase in efficiency for glycoprotein production, which offers a substantial cost advantage for large scale recombinant protein production.

The invention will be further described in the following examples. It should be understood that these examples are for illustrative purposes only and are not to be construed as limiting this invention in any manner.

EXAMPLES

Example 1: Use of 1,3,4-O-Bu$_3$ManNAz to Label Integrin α4 in CHO Cells

Figure 2:
FIG. 2 depicts the result of treating the sample of FIG. 1, lane 3, with PNGAse F and sialidase, with samples then visualized using streptavidin HRP. Notably, specificity of purification was confirmed as imparted via the 1,3,4-O-Bu$_3$-monosaccharide, which was releasable by both PNGAse F and sialidase treatments.
Figure 3:
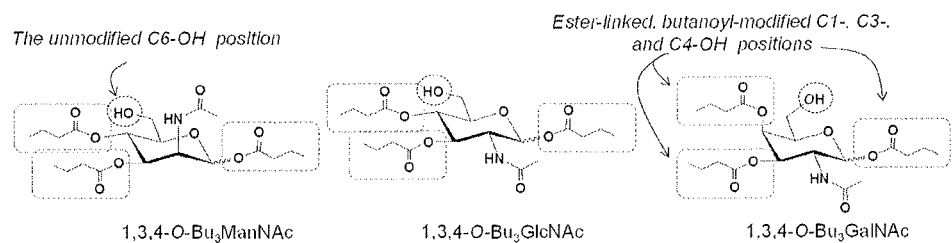
FIG. 3 shows exemplary 1,3,4-O-Bu$_3$ManNAc; 1,3,4-O-Bu$_3$GlcNAc and 1,3,4-O-Bu$_3$GalNAc monosaccharides.
Figure 4:
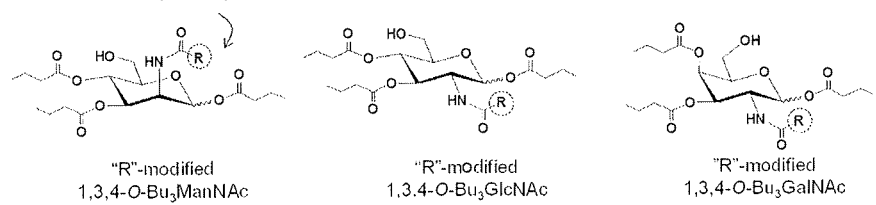
FIG. 4 shows exemplary "R" modified forms of 1,3,4-O-Bu$_3$ManNAc; 1,3,4-O-Bu$_3$GlcNAc and 1,3,4-O-Bu$_3$GalNAc monosaccharides.
Figure 5:
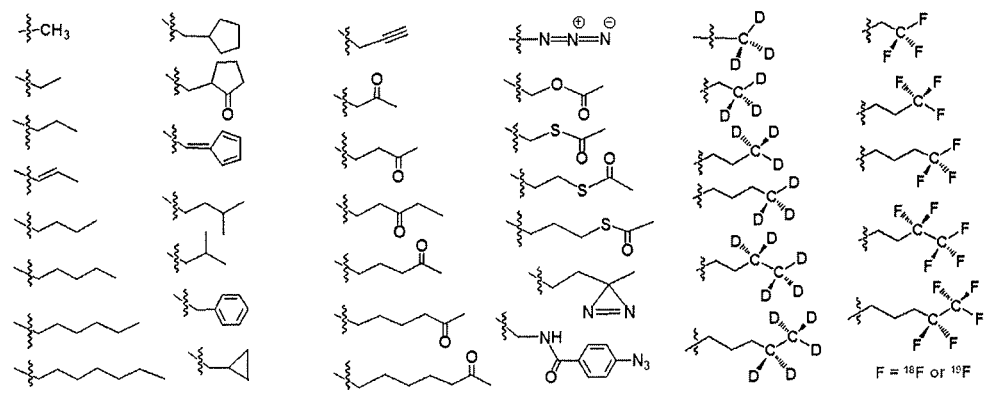
FIG. 5 shows exemplary "R" groups for the structures of the invention.

The use of tri-butanoylated monosaccharides was examined, initially using 1,3,4-O-Bu$_3$ManNAz to label integrin α4 in CHO cells. (CHO cells are a "workhorse" cell line for recombinant glycoprotein production.) As shown in FIGS. 1 and 2, definitive labeling of the human protein integrin α4 stably expressed in a CHO line (Pinco et al. 2002) was obtained.

Example 2: Use of Tri-Butanoylated Compounds in Large Scale Glycoprotein Production Compounds described herein (i.e., 1,3,4-O-Bu$_3$ManNAc, 1,3,4-O-Bu$_3$GlcNAc, 1,3,4-O-Bu$_3$GalNAc) are used in a large scale production process for purpose of providing substantial cost savings over commercially available peracetylated counterparts (e.g., Ac$_4$ManNAc, Ac$_4$GlcNAc, and Ac$_4$GalNAc available from Sigma-Aldrich™ and Invitrogen™). Specific uses include:

Enhancement of antibody sialylation: Increased flux into the sialic acid pathway via 1,3,4-O-Bu$_3$ManNAc was previously shown to increase the degree of sialylation of specific N-glycans by 8-fold or more (Almaraz et al. 2012). Prior studies also showed that various IgG subclasses had a range of sialic acids per protein from 11 to 35% (Jefferis, 1990 #4049). It is newly contemplated that metabolic supplementation using the methods of the invention has the ability to increase even sparsely sialylated species of glycoprotein (e.g., IgG) to fully sialylated glycoforms.

Enhancement of sialylation of recombinant glycoproteins (in general): Although monoclonal antibodies (collectively) are the largest class of recombinant glycoproteins of interest to biotechnology and pharmaceutical industries, the enhanced sialylation of virtually all recombinant glycoproteins by using 1,3,4-O-Bu$_3$ManNAc is expected to increase the degree and homogeneity of sialic acid.

Increased flux into the hexosamine biosynthetic pathway (HBP): By increasing flux into the HBP, which can be accomplished directly through GlcNAc (delivered efficiently by 1,3,4-O-Bu$_3$GlcNAc) or indirectly through GalNAc salvage (via 1,3,4-O-Bu$_3$GalNAc), UDP-GlcNAc levels in a cell are increased. High levels of UDP-GlcNAc ensure adequate levels for N-glycan biosynthesis and, in some cell hosts, allow for a higher degree of branching for N-glycans.

Example 3: Use of Tri-Butanoylated Compounds to Incorporate Additional Chemical Functionalities in Recombinant Glycans The use of tri-butanoylated compounds as described herein in any large scale production process offers significant cost savings over the current commercially available peracetylated hexosamine analogs (e.g., Ac$_4$ManNAz, Ac$_4$GlcNAz, and Ac$_4$GalNAz available from Sigma-Aldrich™ and Invitrogen™). Additional uses for the compounds of the methods of the invention include:

Conjugation of recombinant glycoproteins: In a preferred example, an IgG antibody (having only one N-glycan) is contacted with a chemically functionalized analog such as the azido-modified 1,3,4-O-Bu$_3$ManNAz, thereby installing a chemical tag into the recombinant glycoprotein—this incorporation of a chemical functional group into this oligosaccharide allows for a single, defined site of conjugation. Such site-specific labeling is advantageous (see, e.g., Olafsen et al. 2004, which describes drawbacks of other approaches, e.g., genetic and non-specific chemical modification), and can also enhance imaging, purification and/or delivery of drugs.

Introducing additional chemical properties to recombinant glycoproteins: Because of the ability of glycans to affect the conformation of proteins as well as their assembly, an efficient method to incorporate non-natural sugars into peptides during production processes, as described herein, provides a new option for the protein engineering field. (For creation of proteins with non-natural amino acids, see, e.g., Kwon et al. (2013), and it is noted that protein engineering methods have been undertaken to provide target proteins with altered biophysical properties via new or modified folding motifs or other means to change the flexibility, rigidity, or mechanical strength of the peptide sequence (see, e.g., van Hest et al. 2001).)

Providing additional properties to therapeutic recombinant glycoproteins: Using a non-natural analog such as 1,3,4-O-Bu$_3$ManNAz, such non-natural sialic acids can be introduced into recombinant glycoproteins such as erythropoietin (EPO), thereby improving the pharmacological properties of this commercially important recombinant glycoprotein (e.g., serum longevity (see also Luchansky et al. 2004)).

Example 4: Use of Tri-Butanoylated Compounds to Improve Butyl-Cholinesterase Enzyme Production in CHO Cells In this example, CHO cells expressing butyl-cholinesterase enzyme are contacted with 1,3,4-O-tri-butanoylated compounds as described herein, at sub-millimolar levels (e.g., at 50 µM in the environment of the CHO cells). Expressed butyl-cholinesterase enzyme is harvested. The half life of the butyl-cholinesterase enzyme is assessed and is identified to be significantly greater than the half life of butyl-cholinesterase produced in control CHO cells in the absence of 1,3,4-O-tri-butanoylated compounds as described herein.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

A number of embodiments of the invention have been described. Nevertheless, it will be understood that various modifications may be made without departing from the spirit and scope of the invention. Accordingly, other embodiments are within the scope of the following claims.

What is claimed:

1. A method for producing a glycoprotein possessing increased half-life, reduced toxicity and/or altered immunogenicity comprising: contacting a protein under conditions that allow glycoprotein formation to occur with a compound selected from the group consisting of the following compounds:

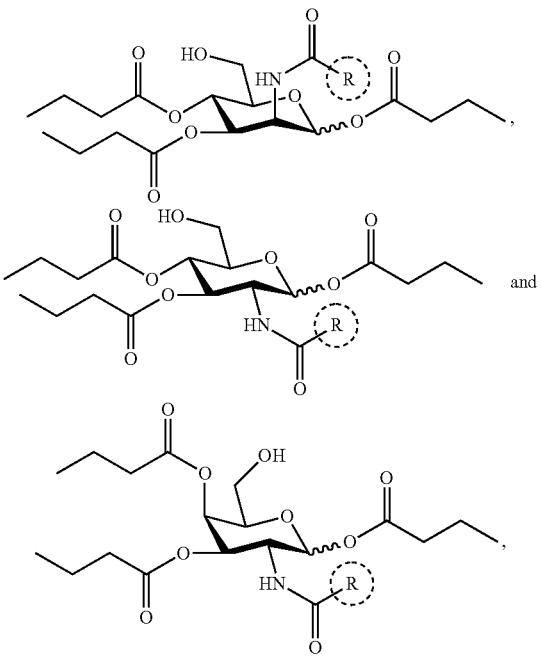

wherein R is selected from the group consisting of

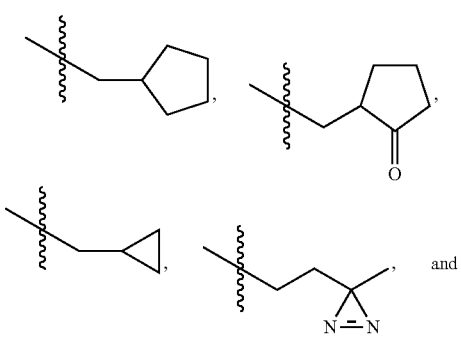

-continued

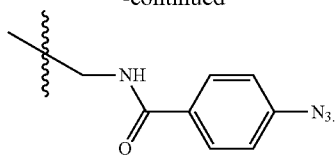

2. The method of claim 1, wherein said glycoprotein is selected from the group consisting of an antibody, an enzyme and a hormone.

3. The method of claim 2, wherein said glycoprotein is an antibody component of intravenous immunoglobulin (IVIG) therapy.

4. The method of claim 2, wherein said glycoprotein is butyl-cholinesterase enzyme.

5. The method of claim 2, wherein said glycoprotein is human growth hormone (HMI).

6. The method of claim 1, wherein said glycoprotein is produced in a mammalian cell.

7. The method of claim 6, wherein said mammalian cell is a Chinese hamster ovary (CHO) cell.

8. The method of claim 1, wherein said glycoprotein possesses increased sialylation as compared to a control glycoprotein not contacted with said compound.

* * * * *